United States Patent [19]

Benazzi et al.

[11] Patent Number: 5,326,928
[45] Date of Patent: Jul. 5, 1994

[54] SEPARATION OF ALIPHATIC PARAFFINS BY ADSORPTION

[75] Inventors: Eric Benazzi, Montesson; Gérard Hotier, Rueil Malmaison; Jean-Marie Basset, Villeurbanne; Agnès Choplin, Villeurbanne; Albert Theolier, Decines; Christophe Nedez, Saint Fons, all of France

[73] Assignee: Institute Francais du Petrole, Rueil Malmaison, France

[21] Appl. No.: 26,791

[22] Filed: Mar. 5, 1993

[30] Foreign Application Priority Data

Mar. 6, 1992 [FR] France .................. 92 02811

[51] Int. Cl.$^5$ .................................. C07C 7/12
[52] U.S. Cl. ...................... 585/820; 585/822; 585/825; 585/830
[58] Field of Search ............ 585/820, 822, 825, 830

[56] References Cited

U.S. PATENT DOCUMENTS 3,755,144  8/1973  Asselin .................. 208/95
4,804,802  2/1989  Evans et al. .............. 585/734

FOREIGN PATENT DOCUMENTS

WO90/09845  9/1990  World Int. Prop. O.

Primary Examiner—Anthony McFarlane
Assistant Examiner—Nhat D. Phan
Attorney, Agent, or Firm—Millen, White, Zelano, & Branigan

[57] ABSTRACT

For the at least partial separation of aliphatic paraffins into at least one effluent comprising the least branched paraffins and at least one effluent comprising the most branched paraffins, use is made of at least one adsorbent bed comprising at least one grafted microporous solid. A preferred use of the invention relates to the treatment of a charge obtained from an isomerization zone, whereby at least one adsorbent bed makes it possible to separate the charge into a first effluent comprising the normal paraffins and a second effluent, and at least one adsorbent bed on which passes the second effluent, comprising at least one grafted microporous solid, making it possible to obtain a third effluent comprising the monomethyl branched paraffins and a fourth effluent comprising the polymethyl branched paraffins.

8 Claims, No Drawings

SEPARATION OF ALIPHATIC PARAFFINS BY ADSORPTION

FIELD OF THE INVENTION

The invention relates to a process for the separation of aliphatic paraffins, which uses at least one bed of adsorbent or adsorbent bed comprising at least one grafted microporous solid permitting the at least partial separation of the least branched paraffins and the most branched paraffins. In a preferred form of the process according to the invention, the separation between the least branched paraffins and the most branched paraffins is total.

BACKGROUND OF THE INVENTION

One of the preferred uses of the invention is in the field of isomerizing gasoline so as to improve the octane number thereof. From the octane number standpoint, it is desirable for the hydrocarbons constituting the gasoline to be as branched as possible. For example, dimethyl butanes have a higher octane number than methyl pentanes. In order to increase the level of polymethyl branched paraffins in the charge from the isomerization zone, it is possible to use molecular sieves selective with respect to the size of the accessible pores and recycle to the isomerization process both the normal paraffins and the monobranched paraffins. Thus, the process according to the invention permitting the at least partial separation of the paraffins from the isomerization process, optionally combined with a recycling to the isomerization process of normal and/or monomethyl branched paraffins, makes it possible to improve the gasoline octane number.

The previously described processes involve the partial or total isomerization of normal paraffins. These processes described in U.S. Pat. No. 4,210,771 (Holcombe), U.S. Pat. No. 3,755,144 (Asselin) and U.S. Pat. No. 4,476,345 (Gray), use zeolites which, due to the diameter of their pores, adsorb the normal paraffins, but not the branched or cyclic products. The most frequently used zeolite is the 5A zeolite, which is a A zeolite, whose substitution cation is calcium, the diameter of its pores being between 3 and 5 Å. It adsorbs normal paraffins, but it does not absorb branched paraffins, not even monomethyl branched paraffin.

U.S. Pat. No. 4,804,802 leads to an improvement to the extent that it describes the use of another molecular sieve permitting the recycling to the isomerization process not only of normal paraffins, but also monomethyl branched paraffins.

The principle of U.S. Pat. No. 4,804,802 is to treat the isomerized hydrocarbon fraction on a molecular sieve bed, whose pores have a diameter equal to or smaller than 4.5 Å and which only adsorbs normal paraffins, allowing the monomethyl branched and obviously the more branched paraffins to percolate. The second molecular sieve bed is constituted by a zeolite, whose pore diameter is between 4.5 and 5.5 Å. This bed adsorbs the monomethyl branched paraffins, whereas the more branched paraffins are not retained and constitute the isomerized fraction with the improved octane number. The first molecular sieve bed described in this patent can be a 5A sieve substituted with calcium, but it is also possible to use other molecular sieves, such as R or T zeolites or even natural zeolites such as chabazite or erionite.

The molecular sieve of the second bed described in the above patent must have a pore size intermediate between that of the calcium 5A zeolite and that of the ZSM5 zeolite, i.e. the pore size is between 4.5 Å×4.5 Å and 5.5 Å×5.5 Å. The zeolite recommended in U.S. Pat. No. 4,804,802 is ferrierite, which e.g. adsorbs monomethyl pentanes. Ferrierite can be used in hydrogen form, but preference is generally given to the form substituted by an alkali metal, an alkaline earth metal or a transition metal. Other adsorbents can be used and are claimed in the above patent and are in particular constituted by aluminophosphates, silicoaluminophosphates and borosilicares. All these adsorbents retain monomethyl branched paraffins and exclude dimethyl branched and polymethyl branched paraffins.

Ferrierite and also the other adsorbents with a pore size between 4.5 Å×4.5 Å and 5.5 Å×5.5 Å have two major disadvantages, namely the small diameter of the pores, necessary for obtaining a selectivity, which necessarily limits the adsorption capacity, as well as the adsorption and desorption kinetics, and the diameter of the pores, which is fixed once and for all for a given adsorbent type, is not of an optimum nature and does not permit a total separation between the monomethyl branched and dimethyl branched paraffin hydrocarbons. Moreover, in the case of ferrierite, it is virtually obligatory from a technical standpoint to use a synthetic ferrierite having far fewer structural defects than natural ferrierite.

SUMMARY OF THE INVENTION

The process according to the invention consists of the at least partial separation of the aliphatic paraffins in a hydrocarbon charge containing 6 to 14 and preferably 5 to 6 carbon atoms per molecule, into an effluent comprising the least branched aliphatic paraffins and an effluent comprising the most branched aliphatic paraffins, said process being characterized by the use of at least one adsorbent bed comprising at least one grafted microporous solid. The use according to the invention of at least one adsorbent bed comprising at least one microporous solid permits the at least partial retention on said solid of the least branched paraffins, i.e. for example normal and/or monomethyl branched paraffins, whereas the most branched paraffins, i.e. for example monomethyl branched and/or polymethyl branched paraffins( i.e. having at least two branches) flow virtually freely through said bed. The least branched paraffins are then recovered by countercurrent scavenging with an eluent.

Thus, the process according to the invention can permit several at least partial separations such as e.g. the following:

the at least partial separation of normal paraffins and other paraffins in the case where the charge comprises normal paraffins, the at least partial separation of monomethyl branched paraffins (and optionally normal paraffins) and other paraffins in the case where the charge has virtually no normal paraffins, the at least partial separation of paraffins incorporating at least one tert. butyl group and other paraffins.

In all cases, the separation is at least partial i.e. it permits the retention on at least one grafted microporous solid of a certain fraction of the aliphatic paraffins which it is wished to separate from the remainder of the charge. The said fraction is between 60 and 100% by weight, preferably between 80 and 100% by weight and in even more preferred manner is 100% by weight, which means that then the retention is total.

Therefore the process according to the invention can be used for the at least partial separation of normal paraffins from branched aliphatic paraffins, as well as between the individual branched aliphatic paraffins, as a function of their degree of branching, by the separation by means of at least one bed of adsorbent comprising at least one grafted microporous solid.

Thus, competitive adsorption tests carried out with mixtures of normal, monomethyl branched and polymethyl branched aliphatic paraffin hydrocarbons revealed either a total adsorption for the normal and monomethyl branched paraffin hydrocarbons and a total rejection for the polymethyl branched paraffin hydrocarbons permitting a total separation, or a relatively high discrimination factor to enable a preparative separation to take place.

Thus, hydrocarbons differ from one another by their kinetic diameter. The latter increases as a function of the number, position and nature of the branches, the n-paraffins having the smallest kinetic diameter. In order that the adsorbent can have a separating power, it is necessary for the adsorbent microporosity to have dimensions intermediate between the kinetic diameters of the different paraffins to be separated. There is no continuous variation of the dimensions of the microporosity of known zeolites. A method making it possible to limit the penetration of the adsorbents to a required space consists of using a wide pore zeolite (larger than the desired screening) and limiting the opening of the micropores by grafting various metalorganic molecules, whose size can be controlled, Thus, in the process of the invention, it is proposed that use be made of grafted microporous solids and preferably grafted zeolites and in even more preferred manner grafted mordenites. This grafting is carried out by chemical reaction and leads to the formation of a metalorganic complex on the surface of the zeolite crystallites. The grafting reaction is of the following type:

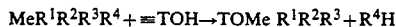

in which:

T stands for an element chosen from within the group formed by Si, Al, Ga, B and Fe, preferably Si, TOH represents a hydroxyl surface group of a silica, a silicaalumina or a microporous solid such as e.g. a zeolite (silicoaluminate), or a microporous aluminophosphate, or a microporous silicoaluminophosphate, or a microporous borosilicate, or a microporous gallophosphate, Me is a metal or an element having a metallic character and is chosen from within the group formed by the following elements: elements of column VA of the periodic classification of elements, e.g. antimony and bismuth, elements of column IVA such as silicon, germanium, tin and lead, elements of column IIIA such as aluminium, boron, gallium, indium and thallium, elements of column IIA such as magnesium and alkaline earth elements and elements of column IIB such as zinc, cadmium and mercury, $R^i$, i being equal to 1,2,3 or 4, is an organic radical such as e.g. methyl, ethyl, propyl, isopropyl, cyclohexyl and phenyl, but it is also possible to use any other known organic radical.

It is largely the steric dimensions of the organic radicals which determines the limitation of the opening of the pores of the microporous solid on which the metalorganic compound is grafted.

The grafting process is described in patent application EP-A-461,171. It is merely pointed out that the reagent is a metalorganic compound $MeR^1R^2R^3R^4$ in which the radicals $R^1$, $R^2$, $R^3$ and $R^4$ can be hydrogen or similar or non-similar organic radicals. Nevertheless, the decomposition stage of the alkyl groups fixed to the metal described in the above patent application is not performed in the present invention, where only the grafting stage is performed. The metalorganic surface complexes formed must be chosen in such a way that they are thermally stable, but are also stable in the presence of oxygen and/or water factor.

Another important factor is the adsorption capacity of the adsorbent for the hydrocarbon in question. In numerous cases, surface grafting does not significantly modify the adsorption capacity with respect to ungrafted mordenite.

Moreover, the careful choice of the grafted metalorganic product (nature and quantity) and also the organic groups carried by the metal (nature and steric dimensions) makes it possible to modify at random and virtually continuously the pore aperture size of the microporous solid. For example, any random grafting of an aforementioned metalorganic product makes it possible to exclude molecules having a tert. butyl group, whilst a total exclusion of dimethyl branched molecules on two adjacent carbons is e.g. obtained by grafting tetracyclohexyl tin on mordenite.

Finally, one of the preferred uses of the process according to the invention is for increasing the level of polymethyl branched paraffins obtained from a charge mainly comprising, i.e. at least 95%, aliphatic paraffins containing 5 to 6 carbon atoms per molecule and preferably a charge from an isomerization zone. Thus, it is possible to use at least one microporous solid making it possible to sample and possibly recycle to the isomerization process both the normal paraffins but also the monomethyl branched paraffins. Thus, when treating a charge mainly comprising aliphatic paraffins containing 5 to 6 carbon atoms per molecule and preferably a charge from an isomerization zone, according to the invention it is possible to proceed in the following way:

at least one adsorbent bed makes it possible to separate the charge into a first effluent mainly comprising the normal paraffins and into a second effluent and then at least one adsorbent bed, onto which passes the second effluent comprising at least one grafted microporous solid, so as to permit the obtaining of a third effluent mainly comprising the monomethyl branched paraffins and a fourth effluent mainly comprising the polymethyl branched paraffins.

The first and third effluents are advantageously recycled to the isomerization process in the case of a charge from an isomerization zone.

The following examples illustrate the invention without limiting its scope.

EXAMPLE 1 according to the invention

A determination takes place of the adsorption capacities of the considered samples for the following hydrocarbons representing different hydrocarbon types: n-hexane, 2-methyl pentane, 2,3-dimethyl butane and isooctane (2,2,4-trimethyl pentane).

The tested adsorbent is a mordenite with a Si/Al ratio of 10. A "blank" test shows that this adsorbent is not selective for the above hydrocarbons and has an adsorption capacity of approximately 12 cm$^3$/100 g.

Following treatment by tetrabutyl tin, SnBu$_4$, the pore aperture size of the adsorbent is reduced by groups ≡Si—O—SnBu$_3$. The adsorption capacities of the aforementioned hydrocarbons in the order given above becomes 7.5–5.4–4.6–0.0 cm$^3$/100 g. A mordenite having a Si/Al ratio of 40 is treated by tributyl tin monohydride SnBu$_3$H and this leads to the following results for the adsorption capacities: 6.2–4.0–3.2–0.0 cm$^3$/100 g.

This demonstrates the existence of a relatively large discrimination between a monomethyl branched hydrocarbon and a dimethyl branched hydrocarbon for which the two branches are consecutive. Moreover, there is a trimethyl branched hydrocarbon exclusion. It would appear that the Si/Al ratio of the mordenite used has no influence.

EXAMPLE 2 according to the invention

The determinations of example 1 are repeated measuring the adsorption capacities for the same hydrocarbons. In a first case use is made of a mordenite of Si/Al ratio of 10, treated with tetramethyl tin and which leads to the formation at the mordenite pore entrance of }Si—O—SnMe$_3$. In this case, the adsorption capacities are respectively 9.5–7.5–4.5–0.0 cm$^3$/100 g which shows a good adsorption selectivity between the monosubstituted hydrocarbon and the disubstituted hydrocarbon, whilst maintaining a reasonable adsorption capacity.

In a second case use is made of a mordenite of Si/Al ratio of 10, treated with tetracyclohexyl tin (SnCy$_4$), which leads to the formation at the mordenite pore entrances of grafted ≡Si—OSnCy entities. In this case 2-methyl pentane is adsorbed and 2,3-dimethyl butane is completely rejected. This is an example of the perfect adsorption selectivity between a monomethyl branched hydrocarbon and a dimethyl branched hydrocarbon for which the two branches are consecutive.

EXAMPLE 3 comparative

Comparison between ferrierite and tetracyclohexyl tin-treated mordenite. This example makes use of two adsorbent beds for treating an equimolar mixture of 2-methyl pentane and 2,3-dimethyl butane. The first is constituted by ferrierite H and the second by tetracyclohexyl tin-treated mordenite. In each case determination takes place of the adsorbent quantity necessary for obtaining 1 g of pure 2,3-dimethyl butane. In the case of ferrierite, it is necessary to use 30 g of bed, whereas in the case of grafted mordenite 5 g of bed are sufficient. This example demonstrates a much higher selectivity of the grafted mordenite.

EXAMPLE 4 comparative

Comparison between ferrierite and tetramethyl tin-treated mordenite. A test similar to that of Example 3 is repeated with an equimolar mixture of n-hexane, 3-methyl pentane and 2,3-dimethyl butane, the two adsorbent beds being constituted by ferrierite H and tetramethyl tin-treated mordenite. A determination takes place with respect to the bed quantity to be used for producing 1 g of effluent not containing n-hexane. In the case of ferrierite, it is necesary to use 18 g of bed, whereas in the case of grafted mordenite it is only necessary to use 10 g of bed. This example shows that the adsorption capacity of grafted mordenite is better than that of ferrierite.

We claim:

1. A process for separating aliphatic paraffins having varying degrees of branching in a hydrocarbon charge containing molecules of 5 to 14 carbon atoms into at least one first effluent comprising less branched paraffins and at least one second effluent comprising more branched paraffins, said process comprising contacting the hydrocarbon charge with at least one adsorbent bed comprising at least one microporous solid having grafted in the pores thereof an organometallic compound of a quantity and shape sufficient to yield pores selective for entry of the less branched paraffins but not the more branched paraffins.

2. Process according to claim 1, wherein the solid is a grafted zeolite.

3. Process according to claim 1, wherein said solid is a grafted mordenite.

4. A process according to claim 1, wherein grafting takes place by the chemical reaction of a organometallic compound on the solid, said compound having the formula MeR$^1$R$^2$R$^3$R$^4$, Me being an element selected from the group consisting of elements of groups of IIA, IIB, IIIA, IVA and VA of the periodic classification of elements and R$^i$, i being equal to 1, 2, 3 or 4, being hydrogen or an organic radical, with the proviso that at least one R group is an organic radical.

5. Process according to claim 4, wherein the element Me is tin.

6. A process according to claim 1, wherein the charge mainly comprises aliphatic paraffins containing 5 to 6 carbon atoms per molecule and wherein the less branched paraffins mainly comprise normal paraffins, said process further comprising withdrawing the effluent comprising the more branched paraffins and contacting said effluent containing the more branched paraffins with another adsorbent bed so as to separate the more branched paraffins into a third effluent mainly comprising monoethyl branched paraffins and a fourth effluent mainly comprising polymethyl branched paraffins.

7. A process according to claim 6, wherein the charge if obtained from an isomerization.

8. Process according to claim 6, wherein the first and third effluents are recycled to said isomerization zone.

* * * * *